(12) United States Patent
Hirsh

(10) Patent No.: US 9,301,678 B2
(45) Date of Patent: Apr. 5, 2016

(54) APPARATUS AND METHOD FOR ASSESSING EFFECTS OF DRUGS BY RECORDING OCULAR PARAMETERS

(71) Applicant: Robert A. Hirsh, Merion Station, PA (US)

(72) Inventor: Robert A. Hirsh, Merion Station, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/206,492

(22) Filed: Mar. 12, 2014

(65) Prior Publication Data

US 2014/0268047 A1     Sep. 18, 2014

Related U.S. Application Data

(60) Provisional application No. 61/786,774, filed on Mar. 15, 2013.

(51) Int. Cl.
| | |
|---|---|
| *A61B 3/14* | (2006.01) |
| *A61B 3/10* | (2006.01) |
| *A61B 3/11* | (2006.01) |
| *A61B 3/113* | (2006.01) |
| *A61B 3/00* | (2006.01) |
| *A61B 5/107* | (2006.01) |
| *A61B 5/11* | (2006.01) |
| *A61B 5/00* | (2006.01) |

(52) U.S. Cl.
CPC .............. *A61B 3/112* (2013.01); *A61B 3/0025* (2013.01); *A61B 3/113* (2013.01); *A61B 3/14* (2013.01); *A61B 5/1075* (2013.01); *A61B 5/1128* (2013.01); *A61B 5/4848* (2013.01); *A61B 5/4863* (2013.01); *A61B 2576/02* (2013.01)

(58) Field of Classification Search
USPC .................................................. 351/200–246
See application file for complete search history.

(56) References Cited

U.S. PATENT DOCUMENTS

| | | | |
|---|---|---|---|
| 7,682,021 B2* | 3/2010 | Sabel | 351/203 |
| 7,773,769 B2* | 8/2010 | Rattan et al. | 382/100 |
| 2006/0114414 A1* | 6/2006 | McGrath et al. | 351/246 |
| 2009/0153796 A1 | 6/2009 | Rabner | |
| 2011/0127101 A1 | 6/2011 | Johnson et al. | |

OTHER PUBLICATIONS

Cross-Disorder Group of the Psychiatric Genomics Consortium, et al., Identification of risk loci with shared effects on five major psychiatric disorders: a genome-wide analysis, Lancet., published online Feb. 28, 2013, 381(9875):1371-1379.

Martinez-Conde, et al., Windows on the Mind, Scientific American, Aug. 2007, 297(2):56-63.

McCamy, et al., The effects of fixation target size and luminance on microsaccades and square-level jerks, PeerJ, Feb. 12, 2013, 1:e9, 1-12.

(Continued)

*Primary Examiner* — Mohammed Hasan
(74) *Attorney, Agent, or Firm* — Howson & Howson LLP

(57) ABSTRACT

The invention is directed to quantification of the effects of drugs on a patient using pupillometric measures. Apparatus and processes for obtaining control and patient measures and deriving relationships from same are provided. The methods of the invention provide doctor quantitative feedback on patient symptoms and on the effects of a drug or dosage of same on a patient, as well as provide assessment capability to patients and law enforcement.

19 Claims, 1 Drawing Sheet

(56) References Cited

OTHER PUBLICATIONS

Stanten, et al., A Statistical Analysis of Pupil Noise, IEEE Transactions on Bio-Medical Engineering, Jul. 1966, vol. BMR-13, No. 3. pp. 140-152.

Stark, et al., Pupil Unrest: An Example of Noise in a Biological Servomechanism, Nature, Sep. 27, 1958, 182(4639):857-858.

Weinhold, et al., Opioid miosis: effects of lighting intensity and monocular and binocular exposure, Drug Alcohol Depend., Jan. 1993, 31(2):177-181.

Zuber, et al., Microsaccades and the velocity-amplitude relationship for saccadic eye movements, Science, Dec. 1965, 150(3702):1459-1460.

* cited by examiner

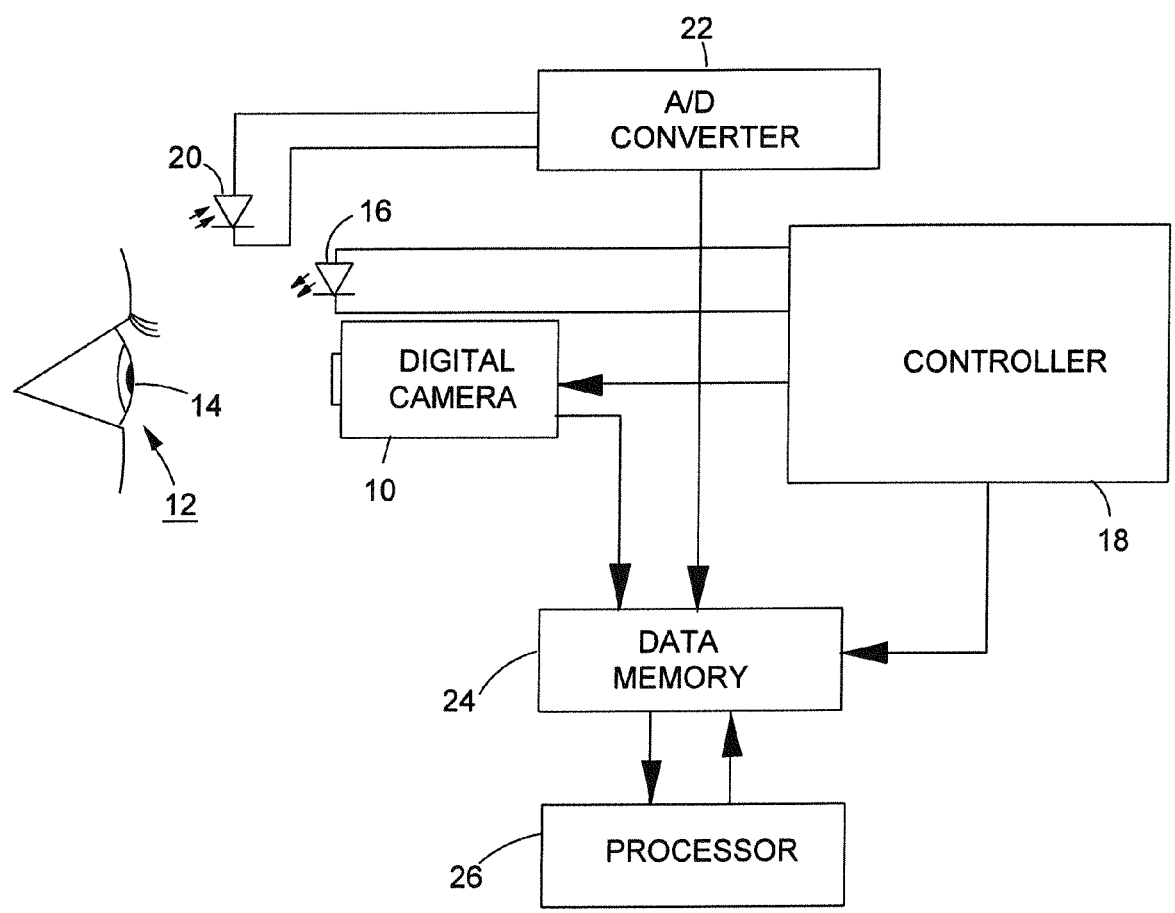

APPARATUS AND METHOD FOR ASSESSING EFFECTS OF DRUGS BY RECORDING OCULAR PARAMETERS

CROSS-REFERENCE TO RELATED APPLICATIONS

This application claims the benefit of the priority of U.S. Provisional Patent Application No. 61/786,774, filed Mar. 15, 2013, which application is incorporated herein by reference in its entirety.

FIELD OF THE INVENTION

This invention relates generally to the assessment of the effects of drugs, and more particularly to the use of multidimensional pupillometry to assess the pharmacodynamic effects of diverse CNS-acting drugs.

BACKGROUND OF THE INVENTION

The human visual system is the product of hundreds of millions of years of highly conserved evolution, allowing for exquisite adaptation to our environment. When a person attends visually to an object in the external world, the object is said to be 'perceived'. The object becomes 'salient' in that person's internal mental horizon. Myriad tightly choreographed neurological and neuromuscular events take place on an autonomic level. Ten extra-ocular muscles must steer and fixate the eyes to achieve binocular vision. The pupil dilates to a size appropriate for the level of ambient illumination. There is 'dither' in the motion of the pupil, whose dilator and constrictor muscles are part of a reflexive negative feedback loop. Clinically, this 'dither' or 'noise' goes by the name 'Hippus'. When the object is close at hand, the gaze converges, and the pupils shrink via the accommodation reflex; the pupil motion become noisier. This entire neurological apparatus is like a finely crafted Swiss chronometer, with many expensive complications.

When a physician gives a patient a drug that crosses the blood-brain barrier, it is like pouring fine sand, heavy motor oil or Gum Arabic into the gear works of a delicate chronometer. Administering a drug cannot fail, in some more or less subtle way, to 'gum up the works'.

Drugs that work in the central nervous systems (CNSs) of conscious patients have been managed solely by subjective clinical assessment. Examples include opioids, for pain, stimulants for attention deficit disorder (ADD)/attention deficit hyperactivity disorder (ADHD), anti-depressants and anti-psychotics, and drugs used for Parkinson's and Alzheimer's Diseases. Particularly in the management of chronic pain, a clinician is unable to verify a patient's continued need for a drug or whether the patient is using all or only a portion of the dosage units prescribed. As a result, opioids among other drugs are diverted from their intended therapeutic use into illegal markets.

SUMMARY OF THE INVENTION

The invention is directed to quantifying the pharmacodynamic effects of pharmaceuticals crossing the blood-brain barrier. Quantification of these effects enhance a clinician's ability to assess efficacy of a treatment by reducing subjectivity, time previously wasted in trial and error, and attendant costs. The invention further permits a clinician to assess and treat patients with barriers to communication, and patients inaccurately (via error or intentionally) reporting symptoms that would traditionally prompt a clinician to adjust dosage or otherwise alter treatment strategy.

One aspect of the invention is an apparatus for recording ocular parameters. The apparatus includes a digital camera for capture of eye measurements; an illumination source to illuminate a patient's eye in a measurable way during capture of eye measurements; a control for adjusting illumination intensity; means for measuring ocular parameters in images of the digital camera; and recording means responsive to the illumination control and the digital camera for generating a record by which at least one parameter is correlated with illumination intensity. Another aspect of the invention further is a process for recording ocular parameters.

Still further included are methods of developing a control based on one or more individuals that are phenotypically normal or abnormal for one or more conditions using ocular parameters obtained as indicated above, and methods for comparing the control to a patient's parameters in order to obtain a diagnosis and gauge the degree of the patient's condition or the level of intervention needed. Comparison of a patient's parameters at one time point to a previous time point, and parallel comparisons to controls, is also useful for adjusting treatment based on patient-specific reaction or tolerance.

Further objects and advantages of the invention will be apparent from the following description when read in conjunction with the drawings.

BRIEF DESCRIPTION OF THE DRAWINGS

FIG. 1 is a schematic block diagram of the apparatus, for recording ocular parameters in accordance with the invention.

DETAILED DESCRIPTION OF THE PREFERRED EMBODIMENTS

Quantitative measurement of the pharmacodynamic effects of drugs is needed in clinical practice. The physical and methodological embodiments described herein take advantage not only of variations in pupillary diameter with changing levels of illumination, but also of other involuntary changes of the pupil diameter (Hippus), and movements of the entire globe of the eye (micosaccades).

The term clinician as used herein includes a medical researcher, doctor, physician, physician's assistant, nurse, mental health professional, psychiatrist, or other medical professional, the terms being used interchangeably unless expressly noted or the context provides otherwise. For example, the term clinician is intended to be limited to those medical professionals having the authority to prescribe drugs where the context requires, e.g., in a method that includes prescribing a specific drug at a specific dosage or modifying the drug or dosage.

The terms condition, disease, syndrome, injury, and disorder are used interchangeably throughout, unless otherwise provided for expressly or in context.

The terms compound, drug, central nervous system drug, CNS drug, substance, medication, and metabolite, are all used interchangeably to encompass any substance which crosses the blood-brain barrier, unless otherwise provided for expressly or in context. Still further included are agents (including the interchangeable terms defined in this definition in their colloquial usage (i.e., not specific to blood brain barrier passage) that influence, directly or indirectly, a substance.

The terms effect, pharmacodynamic effect, psycho-pharmacological effect, and pharmacological effect are used interchangeably to encompass the impact of a drug on a subject and more specifically on its central nervous system or portion thereof, unless otherwise provided for expressly or in context.

The terms eye, eye ball, and globe of the eye, are intended to have the same meaning unless a distinction is made herein.

The term subject as used herein is intended to encompass a mammalian subject, including a human subject, and is used interchangeably with the term individual or patient herein, unless expressly indicated or the context provides otherwise.

Measures and Data Processing

Hippus is also referred to as pupillary noise, or noise. It is the low frequency (f=0.2 Hz-3 Hz) spontaneous motion of the pupil at constant ambient illumination. It is caused by the autonomic 'tug-of-war' between the dilator and constrictor muscles of the pupil. In other terms, the tug-of-war is between the sympathetic and parasympathetic nervous systems. This noise may be measured by the standard deviation (SD) of the pupillary area (A) over time (T).

Microsaccades are short (period=5-10 msec), angular motions (θ=about 2 to 3 minutes, e.g. 2.25 minutes, of arc) of the entire globe of the eye in any direction $\emptyset$ ($\emptyset$=arctan Δy/Δx), with an angular velocity (ω) of about 5 to about 10, e.g. 7.7, degrees/second. Microsaccades are autonomic and involuntary, and can occur even as a gaze is fixed. It is believed that they serve to prevent neural adaptation of the rod and cone sensory cells in the macula of the retina. Without microsaccades, it is believed that the external world would quickly fade to black from subject's perspective.

Pupillary area may be determined by any conventional means. In one embodiment, pupil area is determined by counting the pixels of a digital image of the pupil and multiplying it by the calibrated area per pixel. This may be done by an image processor or by other means known in the art. In an embodiment where a change of pupillary diameter is measured, the number of pixels may be used without multiplication by a calibration factor.

Pupillary diameter (D) may be expressed as a function of time (t) over a fixed luminance (L) with the pupil focused on an object at distance (S).

$$D(L,S)=[4(\bar{A}/\pi)]^{1/2} \quad \text{(Equation 1)}$$

wherein $\bar{A}$ is the average pupillary area A. The diameter D of a pupil fixed at infinity, over a range of ambient luminance L, may be summarized as $$D(L)=D_0-k1*\ln(L) \quad \text{(Equation 2)}$$

where k1 is the slope of the pupil diameter vs. ln (luminance) curve as a function of time. Alternatively, the average pupil area $\bar{A}$ itself decreases linearly with ln (luminance), so we can write $$\bar{A}(L)=\bar{A}_0-k1'*\ln(L) \quad \text{(Equation 2a)}$$

Pupillary noise (Hippus) may be expressed as the standard deviation of A(t) from $\bar{A}$. Since pupillary noise SD(L,S) increases linearly as average pupillary area $\bar{A}$ decreases, $$SD(\bar{A})=(SD)_0-k2*(\bar{A}) \quad \text{(Equation 3)}$$

where $\bar{A}$ is average area of the pupil and k2 is the slope of the standard deviation of the average pupil area vs. average pupil area curve.

In addition to area as a function of luminance L, and the standard deviation of average area $\bar{A}$ as a function of $\bar{A}$, we can calculate the standard deviation of $\bar{A}$ as a function of L by the formula:

$$SD(\bar{A})=(SD)_0+k4*\ln(L) \quad \text{(Equation 3a)}$$

where $(SD)_0$ is 0 when L is at $L_0$. $L_0$ is a luminance approaching limit 0.

There is a unit logarithmic increase in the ambient luminance (ln(L)) that will cause a given linear increase in the noise SD($\bar{A}$), which in turn results in a given unit linear decrease in pupil area $\bar{A}$. It does not matter how the decrease in $\bar{A}$ is accomplished. It can be accomplished by increasing illumination or by accommodation to an object near to the observer via the accommodation reflex. In either case, the pupils reflexively shrink, that is, $\bar{A}$ decreases. As long as $\bar{A}$ decreases by the same amount on account of either mechanism, the same unit increase in noise (SD($\bar{A}$)) results. In other words, the partial derivative δSD($\bar{A}$)/δ$\bar{A}$ is nearly the same whether the lighting level is increased or an object is held close to the patient's face. A difference in the response δSD($\bar{A}$)/δ$\bar{A}$, depending on whether the response is provoked by a change in illumination or by accommodation to a near object, can be utilized to examine the effects of CNS-acting drugs and in the diagnosis of neurological disease.

In the practice of the invention, one, two, three, four, or all of L, ln(L), D, t, and $\bar{A}$ are calculated and serve as a non-invasive pharmacodynamic index for drugs acting in the central nervous system. In a further embodiment, the partial derivative of the standard deviation of pupil area SD(A) as a function of ln(L), δ[SD(A)]/δ[ln(L)], serves as another index, or dimension, of the state of the visual reflexes.

Microsaccades can be measured by electronically drawing two mutually perpendicular tangents to the limbus, i.e., the circular border between the iris and the sclera, on a video image of the eye. One tangent can be horizontal while the other is vertical. Displacement of the tangent lines in the horizontal (ΔX) and vertical direction (ΔY), and the time interval over which the microsaccades occur, are measured from one video frame to the next.

A measure of the angular displacement of the eye is determined from the horizontal and vertical displacements according to the following equation:

$$\theta i=[(\Delta X^2+\Delta Y^2)^{1/2}]/r \quad \text{(Equation 4)}$$

where θi, in radians, is the angular displacement of the ith microsaccade, and r is the radius of the globe of the eye.

The angular velocity may be expressed as $$\omega i=[(\Delta X^2+\Delta Y^2)^{1/2}]/r\Delta t \quad \text{(Equation 5)}$$

where Δt is the time interval over which the microsaccade occurs. The frequency f of microsaccades is given by the formula $$f=1/\Delta t. \quad \text{(Equation 6)}$$

One, two, or all of f, θ, and ω can be calculated and can serve as a non-invasive pharmacodynamic index for drugs acting in the central nervous system. Further, the relationship between θ and ω may be expressed as:

$$\ln(\omega)=k3*\ln(\theta). \quad \text{(Equation 7)}$$

Tracking k1, k2, and/or k3 in formulae:

$$D(L)=D_0-k1*\ln(L) \quad \text{(Equation 2),}$$

$$SD(\bar{A})=(SD)_0-k2*(\bar{A}) \quad \text{(Equation 3), and}$$

$$\ln(\omega)=k3*\ln(\theta) \quad \text{(Equation 7)}$$

will quantify 'decoupling' that occurs between D and L in Equation 2, SD and (L,S) [$\bar{A}$ being a function of (L,S)] in Equation 3, and ω and θ in Equation 7.

In one embodiment, curve fitting software can calculate {k1}, {k1, k2}, or {k1, k2, k3} when the subject's gaze is fixed on a point along a plane at infinity or otherwise in the distance, e.g., S=∞, or when fixed at S=a point along a plane near the subject's eye ('near-gaze'). Optionally k1' can be substituted for k1. k4 may also be included. In a further embodiment, the parameters for both near-gaze and far-gaze are fitted together in a 2×3 matrix. In still further embodiments, measurements from further distances may be included. Still further, k factors addressing the relationship of one, two, three, or more of the measured variables identified in this application may be included.

In a further embodiment, the curve-fitting parameters, or matrix of same, may be used to create a weighted average varying along a number line, e.g., 1 to 100, which may be used to indicate pharmacological effect. This may be done in the manner used in 'BIS' processed EEG monitors for the assessment of consciousness of a patient undergoing anaesthesia.

The parameters may also be used to generate vectors, including Cartesian vectors, in the number of dimensions needed to encompass the parameters. For example, one Cartesian vector can provide the location of a point in a vector space with three axes, {k1, k2, k3} at a near distance ('gaze with near accommodation' space), and a second vector for the same constants k at a far distance ('gaze at infinity' space). One may also combine two, three, four, or five of $\overline{A}$, SD, ln(L), ω, and θ. In some embodiments, a CNS-active agent will provide an observable effect in one 'space' and not the other, and in other embodiments will provide an observable effect in both.

One of skill in the art will be able to use mathematics and software to convert/map control and subject data inputs into outputs useful for comparison, diagnosis, and treatment by a clinician. LABVIEW (National Instruments Corporation, Austin, Tex.) and ORIGIN (Origin Lab Corporation, Northampton, Mass.) software may be used. However, the data collection and analysis software used is not intended to be a limitation of the invention.

Measuring Means and Process

An apparatus for recording ocular parameters is depicted in FIG. 1. The apparatus includes a digital camera 10 for capturing a sequence of images of a portion of at least one eye 12 of a subject and converting the images to a recordable digital format. Although it is possible to measure eye movement and rate of movement from an image that includes only parts of the limbus, i.e., the circular border between the iris and the sclera, if measurements of pupil diameter or changes in pupil diameter are to be made, either with or without making measurements of eye movement, the portion of the eye captured by the digital camera should include the pupil 14. In further embodiments, one camera, or two cameras arranged to operate at the same time, is positioned to capture images of both eyes of a subject as otherwise described herein.

The digital camera may be a 'still' image camera or a 'video' camera, as those terms are commonly used. However, the digital camera should be capable of capturing a number of images per second providing a basis for a statistically significant measurement of the change in any of the measurable variables identified herein, e.g., pupillary area, change in pupillary area (hippus), angular displacement of the eye (θ), and change in θ (microsaccades). In one embodiment, the digital camera will be capable of capturing at least 1000 frames per second (fps). However, in other embodiments, 30 to 500 fps, 30 fps, 50 fps, 100 fps, or 500 fps may be used. The number of frames per second acceptable for development of a control/standard, diagnosis, or evaluation of a treatment, will vary depending on the parameters of interest and whether the parameters are being taken for development of a control or for diagnosis/evaluation.

The apparatus also includes a source of illumination in the visible range of wavelengths, the illumination source being arranged in relation to the camera to illuminate a patient's eye when the camera is positioned to record images of the patient's eye. The illumination source may be any known in the art that is safe with close proximity to the eye of a mammalian subject. In the embodiment depicted in FIG. 1, the light is produced from a light emitting diode (LED) 16. In another embodiment, the light is produced from a fluorescent or compact fluorescent bulb.

The illumination source must be such that it may be operatively connected with a control 18 for varying the intensity of illumination emitted by the source. The control 18 can be a software-implemented control using a microprocessor, a firmware-implemented control using a microcontroller, or any of various other forms of controls.

The control may be operative to cause the illumination emitted by said source to vary in steps, the illumination in each of said steps being constant over a predetermined interval of time. The control may be operative to cause the illumination emitted by the source to increase monotonically in steps, the illumination in each of the steps being constant over a predetermined interval. The control may also be operative to cause the illumination emitted by the source to increase monotonically in steps from a minimum level to a maximum level, and to decrease monotonically in steps from the maximum level to the minimum level, the illumination in each of the steps being constant over a predetermined interval.

In one embodiment, the apparatus is enclosed to limit entry of ambient light, and the apparatus contains a screen of adjustable illumination. The video screen may display 'still' images or video. The images or video may be displayed in such a way as to appear to the subject as near (e.g., at a distance of 1, 5, 10, or 100 centimeters) or far (e.g., at a distance of 100 meters, 1000 meters, or some farther distance approaching infinity).

The apparatus of FIG. 1 includes a photometer arranged in relation to the illumination source 16 to measure the intensity of the illumination emitted by said source. The photometer, which includes a sensor 20, e.g., a photodiode, and an analog-to-digital converter 22, provides an output in digital format corresponding to the measured illumination intensity. The digital output of the A/D converter (or digitizer) 22 is recorded in a digital data memory 24 along with the digitized image captured by camera 10. The images and the illumination levels as measured by the photometer are correlated in the memory so that the illumination levels can be correlated with each of several ocular parameters derived from the image, e.g., pupil diameter, Hippus, or microsaccades. The recordation of the output of the photometer in data memory 24 is responsive to controller 18.

The apparatus includes a processor 26, which is programmed to derive, from the recorded images in memory 24, measurements of at least one parameter from among pupil area, pupillary hippus, angular displacement of the eye, and the rate of the angular displacement.

The processor may also be programmed so that, in response to the control and to the digital camera it generates a record in which the at least one parameter is correlated with the intensity of the illumination emitted by light source 16 and detected by the photometer composed of detector 20 and analog-to-digital converter 22. The record in which the at least one parameter is correlated with illumination intensity can be stored in data memory 24 or in a separate memory (not shown).

Plural parameters from among pupil area, pupillary hippus, the angular displacement of the eye, and the rate of angular displacement of the eye can be measured, recorded and correlated with illumination intensity in memory 24 or in a separate memory.

Also provided are processes for recording ocular parameters. One process includes exposing an eye of a subject (including a human or other mammalian subject) to illumination in the visible range of wavelengths, and changing the intensity of the illumination in steps, maintaining the intensity in each of the steps constant over an interval sufficient to capture a sequence of images of a portion of the eye, the portion including at least the pupil of the eye.

While exposing the eye to illumination and changing the intensity of the illumination in steps, in each step a sequence of images of the portion of the eye is captured, and the images are converted into a recordable digital format.

The exposing and image-capturing steps are performed while the individual is focusing visually on a distant object (either actually or via visual illusion within a video display), and also while the individual is focusing visually on a near object (either actually or via visual illusion within a video display).

The process further includes measuring in the images at least one parameter from among pupil area, pupillary hippus, angular displacement of the eye, and the rate of angular displacement; and generating a record in which the at least one parameter that was measured is correlated with the intensity of the illumination.

In measuring, plural parameters from among pupil area, pupillary hippus, the angular displacement of the eye, and the rate of angular displacement may be measured, and the plural parameters may be correlated with the intensity of illumination in the record-generating step.

To eliminate possible hysteresis in the pupil area and pupil noise vs. In (luminance) curve, the intensity of the illumination emitted by the illumination source may be increased monotonically from a minimum level to a maximum level, and decreased monotonically from the maximum level to the minimum level, in steps.

The exposing, intensity-changing, measuring, and record-generating steps may be carried out on the individual both before and after administration to the individual of a central nervous system-acting drug.

Methods

The invention provides for methods of preparing control measures from the impact of a drug on a population of patients having or not having a given condition, or the impact of a drug on a population diagnosed with or not being diagnosed with a given condition. The characteristic change or arc of a vector described by (k1, k2, k3) or (k1', k2, k3) for any substance (defined above) in a substance-specific fashion.

The controls may also include measures of the same populations without any administration of a drug. The controls can also be useful in determining the time in which a subject or population of subjects metabolizes the drug.

Similarly, methods are provided for comparing parallel measures of a subject to the control for the purpose of diagnosis or for assessing the impact of the dosage of a drug on the subject.

In methods for the establishment of controls, the population(s) are measured using the means and processes described. The data obtained are processed using the data processing described, and in further embodiments variables k1, k2, k3, and other parallel variables are determined. The result of processing, whether numeric, graphic, or otherwise, is then used for comparison with a subject.

In methods for assessing the impact of a drug or dosage thereof on a subject, data are obtained and processed as described for controls. The processed data, whether numeric, graphic, or otherwise are then compared to control data.

The method and apparatus of the invention permit a physician to diagnose a patient and prescribe suitable medications and to adjust dosage or medication consistent with intended outcomes. The process is analogous to the process used to adjust the depth of anesthesia. That is, a patient under anesthesia is continuously monitored by EEG. Data on brain activity obtained is expressed numerically on a scale of 1 to 100 in a bispectral index (BIS). By reviewing the BIS measure, a physician can adjust depth of anesthesia of the patient based on appropriate values obtained from prior anesthetization of a population of subjects ('controls') even though a particular patient under anesthesia will be unable to vocalize his or her actual response in a meaningful way. The methods of the invention operate in a similar way, enabling the physician to diagnose, prescribe and adjust based on measurements taken of a particular patient, and on a database derived from similar measurements taken on numerous patients and controls.

The methods of the invention further includes self-assessment of a subject using a portable device, such as a "smartphone," e.g. an iPhone™ device, having a camera and an installed application that can process image data as described herein and compare it to stored control data of the patient or a wider control population. For example, a contemplated method provides patients with ADD/ADHD an indication that their stimulant mediation is wearing off, and that they need to take a small dose of short acting agent. Such a method may be accompanied by an alarm integrated within the device and programming for same.

Other methods of the invention include the assessment of a patient to determine use of a drug, use at the prescribed dosage, or tolerance to a drug. The invention also contemplates the use of a portable device for law enforcement purposes, and the use of fixed device interlocks, using the technology of the invention. Still other methods of the invention apparent to the skilled artisan are contemplated and intended to be encompassed by the application.

Conditions that are assessed according to the invention include, but are not limited to cancers, mental disorders, metabolic disorders. Conditions include those of the circulatory, digestive, endocrine, immune, lymphatic, limbic, musculoskeletal, nervous, reproductive, respiratory, and urinary systems.

Any condition having a neurological manifestation is intended to be assessed according to the invention. These include any condition having global neurological illness, as well as any condition having global neurological symptoms (e.g., mental illness). The invention empowers mental health professionals to rationally choose and manage psycho-pharmacotherapeutic agents in the treatment of mental health conditions.

Specific conditions that are assessed include attention deficit disorder (ADD), attention deficit hyperactivity disorder (ADHD), autism, anxiety, depression, mania, fatigue, chronic fatigue syndrome, insomnia, schizophrenia, obsessive compulsive disorder (OCD), post-traumatic stress disorder (PTSD), concussion, anorexia nervosa, bipolar disorder, memory deficit, amnesia, agnosia, Alzheimer's disease, traumatic brain injury (TBI), headache, dementia, epilepsy, hyperthymestic syndrome, Huntington's disease, Parkinson's disease, tertiary syphilis, alcoholism, and Wernicke-Korsakoff's syndrome.

With respect to traumatic brain injury (TBI), including that caused by concussive impact, the invention is useful in assessing the injury. These concussive impacts include those resulting from improvised explosive devices (IEDs). Also included is the assessment of concussions in football, hockey, baseball, basketball, and soccer ('futbol'), and other sports. These include professional leagues such as the National Football League (NFL), the National Hockey League (NHL), National Basketball Association (NBA), Major League Baseball (MLB) and Major League Soccer (MLS), as well as 'minor' and collegiate (NCAA) competition. This assessment may include 'sideline' or 'locker room' assessment using a device described herein. The invention provides a metric of the extent to which the involved neurological pathways are deviated from normal function.

Conditions that are assessed further include multiple sclerosis, Tourette's, amyotrophic lateral sclerosis (ALS), cerebral palsy, restless leg syndrome, and spasticity. Still further included are liver failure, kidney failure, type I diabetes, type II diabetes, gestational diabetes, back pain, chronic pain, fibromyalgia, hypercorticolism (Cushing's syndrome), menopause, and obstructive sleep apnea. Cardiovascular conditions that are assessed include stroke, peripheral arterial disease, arterial plaque, hypertension, and high cholesterol. In further embodiments, the invention is used to assess bacterial and is used to assess viral infections.

Paraneoplastic syndromes and paraneoplastic neurological diseases (PNDs) may also be assessed according to the invention, including those of the lung, breast, or ovary. These diseases can cause dizzyness, ataxia, nystagmus, loss of motor coordination, visual problems, sleep disturbances, dementia, and seizures.

Cancers that are assessed include lymphoma, melanoma, sarcoma, lung cancer, lymphoma, non-Hodgkin lymphoma, large cell lymphoma, small cell lymphoma, large cell carcinoma, small cell carcinoma, and mesothelioma. Assessment of other cancers, e.g., focal cancers, is intended to be encompassed by the invention, where a substance that is a signature for the cancer crosses the blood-brain barrier.

The invention further includes assessing the presence, or level in the blood of, glucose, LDL cholesterol, HDL cholesterol, triglycerides, ammonia, metabolites, including urea, and toxins. It may also include assessing blood pressure, particularly for self-assessment. For newborn infants, assessment of bilirubin is performed, e.g., in kernicterus.

The invention may also be used to evaluate the level of a drug in a subject. Drugs that are evaluated include, but are not limited to psychoactive drugs, including sedatives and hypnotics, stimulants, opiates, and hallucinogens and psychedelics. Included are heroin, morphine, codeine, thebaine, and semi-synthetic opiates including hydrocodone, hydromorphone, oxycodone, and oxymorphone. Also included are antibiotics, including cephalosporins (including cefotaxime, ceftizoxime, ceftriaxone, and cefepime) ampicillin, efotaxime, gentamicin sulfate, penicillin G, and vancoymcin.

In pain management (post-operative, cancer, chronic non-cancer), opioids (among others), are evaluated to quantify effect in reducing or eliminating pain on an individualized basis. These methods reduce the risk of dependence and addiction.

Other drugs which are evaluated include performance enhancing drugs (PEDs), i.e., 'doping.' For example, steroids, including anabolic steroids, xenoandrogens, beta-2 agonists, selective androgen receptor modulators (SARMs), testosterone, epitestosterone, and human growth hormone. Another PED which is assessed is erythropoietin (EPO). Others include stimulants such as caffeine, cocaine (benzoylmethylecgonine), amphetamine, methamphetamine, and methylphenidate (RITALIN). Ketamine and PCP [Phencyclidine; 1-(1-phenylcyclohexyl)piperidine] are also assessed. Still others include painkillers such as NSAIDs (e.g., ibuprofen, narcotics), and sedatives such as delta-9 tetrahydrocannabinol (THC, e.g., from marijuana), alcohol, diazepam, and propanolol. Still other mass builders, stimulants, painkillers, sedatives, diuretics, blood boosters, and masking drugs are known in the art and are intended to be encompassed within the scope of those drugs assessable according to the invention.

Still any other drug (i.e., a compound capable of crossing the blood-brain barrier or influencing a compound capable of same) is assessed according to the methods described herein.

All documents recited above are incorporated herein by reference. Numerous modifications and variations are included in the scope of the above-identified specification and are expected to be obvious to one of skill in the art. Such modifications and alterations are believed to be within the scope of the claims appended hereto.

What is claimed is:

1. An apparatus for recording ocular parameters comprising:
   a digital camera for capturing a sequence of images of a portion of an eye and converting said images to a recordable digital format;
   a source of illumination in the visible range of wavelengths, said illumination source being arranged in relation to said camera to illuminate a patient's eye when the camera is positioned to record images of the patient's eye;
   a control operatively connected to said source of illumination for varying the intensity of illumination emitted by said source;
   means for measuring in said images at least one parameter from among pupil area, pupillary hippus, angular displacement of the eye, and the rate of said angular displacement; and
   recording means responsive to said control and to said digital camera for generating a record in which said at least one parameter is correlated with the intensity of said illumination.

2. An apparatus according to claim 1, in which said portion of the eye includes the pupil of the eye.

3. An apparatus according to claim 1, including a photometer arranged in relation to said source of illumination to measure the intensity of the illumination emitted by said source, and providing an output in digital format corresponding to the measured illumination intensity, wherein said recording means is responsive to said output provided by the photometer, and thereby responsive to said control.

4. An apparatus according to claim 1, wherein said control is operative to cause the illumination emitted by said source to vary in steps, the illumination in each of said steps being constant over a predetermined interval of time.

5. An apparatus according to claim 1, wherein said control is operative to cause the illumination emitted by said source to increase monotonically in steps, the illumination in each of said steps being constant over a predetermined interval.

6. An apparatus according to claim 1, wherein said control is operative to cause the illumination emitted by said source to increase monotonically in steps from a minimum level to a maximum level, and to decrease monotonically in steps from said maximum level to said minimum level, the illumination in each of said steps being constant over a predetermined interval.

7. An apparatus according to claim 1, wherein said means for measuring in said images at least one parameter measures plural parameters from among pupil area, pupillary hippus, the angular displacement of the eye, and the rate of said angular displacement; and wherein said recording means generates a record in which said plural parameters are correlated with the intensity of said illumination.

8. A process for recording ocular parameters comprising:
exposing an eye of an individual to illumination in the visible range of wavelengths, and changing the intensity of said illumination in steps, maintaining the intensity in each of said steps constant over an interval sufficient to capture a sequence of images of a portion of said eye;
while exposing said eye to illumination and changing the intensity of said illumination in steps, capturing in each step a sequence of images of said portion of the eye, and converting said images to a recordable digital format;
carrying out said exposing and image-capturing steps while said individual is focusing visually on a distant object, and also while said individual is focusing visually on a near object;
measuring in said images at least one parameter from among pupil area, pupillary hippus, angular displacement of the eye, and the rate of said angular displacement; and
generating a record in which said at least one parameter is correlated with the intensity of said illumination.

9. The process according to claim 8, wherein the intensity of said illumination is measured by means of a photometer, and wherein, in said record-generating step said at least one parameter is correlated with the intensity of said illumination as measured by means of said photometer.

10. The process according to claim 8, wherein the intensity of the illumination emitted by said source is increased monotonically from a minimum level to a maximum level, and decreased monotonically from said maximum level to said minimum level, in said steps.

11. The process according to claim 8, wherein, in said measuring step, plural parameters from among pupil area, pupillary hippus, the angular displacement of the eye, and the rate of said angular displacement are measured, and wherein, in said record-generating step said plural parameters are correlated with the intensity of said illumination.

12. The process according to claim 8, wherein said exposing, intensity-changing, measuring, and record generating steps are carried out on said individual both before and after administration to said individual of a central nervous system-acting drug.

13. A method for assessing the impact of a drug or dosage thereof on a subject, comprising performing the process according to claim 8 and comparing said record to a control.

14. The method according to claim 13, wherein the control comprises one or more earlier measurements of said at least one parameter of the subject.

15. A method for assessing the impact of a drug or dosage thereof on a subject, comprising: measuring in an eye of said subject at least one parameter from among, pupillary hippus, and the rate of angular displacement of the eye, wherein the measurement of said at least one parameter is obtained while said subject's gaze is fixed on a single object in the absence of other visual stimuli; and
comparing the measurement of said at least one parameter to a control;
further comprising a second step of measuring in said subject at least one parameter from among pupillary hippus and the rate of angular displacement of the eye, wherein the measurement of said at least one parameter is obtained while said subject's gaze is fixed on said single object in the absence of other visual stimuli, and wherein during said second step of measuring said eye of said subject is exposed to a different intensity of illumination than during the first step of measuring.

16. The method according to claim 15, wherein the control comprises one or more earlier measurements of said at least one parameter of the subject.

17. The method according to claim 15, comprising measuring pupillary hippus in said subject.

18. The method according to claim 15, comprising measuring angular displacement of the eye in said subject.

19. The method according to claim 15, wherein the drug is a performance enhancing drug (PED).

* * * * *